United States Patent
Patel et al.

(10) Patent No.: US 9,486,590 B2
(45) Date of Patent: Nov. 8, 2016

(54) AUTOMATIC PURGING OF AIR FROM A FLUID PROCESSING SYSTEM

(71) Applicant: Fenwal, Inc., Lake Zurich, IL (US)

(72) Inventors: Amit J. Patel, Algonquin, IL (US); Melissa A. Thill, Kenosha, WI (US); Kathleen M. Higginson, Mount Prospect, IL (US)

(73) Assignee: Fenwal, Inc., Lake Zurich, IL (US)

( * ) Notice: Subject to any disclaimer, the term of this patent is extended or adjusted under 35 U.S.C. 154(b) by 166 days.

(21) Appl. No.: 14/500,529

(22) Filed: Sep. 29, 2014

(65) Prior Publication Data

US 2016/0089504 A1 Mar. 31, 2016

(51) Int. Cl.
*A61M 1/36* (2006.01)
*A61M 1/38* (2006.01)
(Continued)

(52) U.S. Cl.
CPC ............. *A61M 5/365* (2013.01); *A61M 1/30* (2013.01); *A61M 1/303* (2014.02); *A61M 1/3496* (2013.01); *A61M 1/3626* (2013.01); *A61M 1/3627* (2013.01); *A61M 1/3643* (2013.01); *A61M 1/3646* (2014.02); *A61M 5/14* (2013.01); *A61M 5/36* (2013.01); *A61M 1/262* (2014.02); *A61M 1/342* (2013.01); *A61M 1/3672* (2013.01);
(Continued)

(58) Field of Classification Search
CPC ...... A61M 1/30; A61M 5/14; A61M 1/3496; A61M 1/3626; A61M 5/365; A61M 1/303; A61M 1/3646; A61M 5/36; A61M 2205/3375; A61M 2205/3393; A61M 1/262; A61M 2202/0413; A61M 2202/0021; A61M 2005/1403; A61M 2205/3389; A61M 1/3672; A61M 2205/07; A61M 1/342; A61M 1/3627; A61M 1/3629; A61M 1/3455; A61M 1/3465; A61M 1/3643; A61M 1/3624; A61M 1/302; A61M 1/3424; A61M 1/3621
See application file for complete search history.

(56) References Cited

U.S. PATENT DOCUMENTS 250,868 A 12/1881 Abbott
927,476 A 7/1909 Barker
(Continued)

FOREIGN PATENT DOCUMENTS

CH 296007 1/1954
DE 1806654 5/1970
(Continued)

OTHER PUBLICATIONS

Extended European Search Report and Written Opinion for EP 15 18 7181, dated Feb. 19, 2016.

*Primary Examiner* — Adam Marcetich
(74) *Attorney, Agent, or Firm* — Cook Alex Ltd.

(57) ABSTRACT

Systems and methods are provided for processing a fluid and then returning processed fluid and/or replacement fluid to a fluid recipient. The returning fluid is monitored to detect air therein and, if air is detected, steps are taken to automatically purge the air from the returning fluid without requiring the intervention of a system operator. The system may respond to detected air by pumping the processed fluid and/or replacement fluid away from the fluid recipient and into a processed fluid reservoir, where the air is purged from the processed fluid and/or replacement fluid. Thereafter, the weight of the processed fluid reservoir may be checked to confirm that sufficient fluid has been pumped back into the reservoir to remove the air. After it has been confirmed that the air has been purged from the fluid, the system may resume pumping the fluid toward the fluid recipient.

20 Claims, 6 Drawing Sheets

(51) Int. Cl.
    *A61M 5/36* (2006.01)
    *A61M 1/30* (2006.01)
    *A61M 5/14* (2006.01)
    A61M 1/34 (2006.01)
    A61M 1/26 (2006.01)

(52) U.S. Cl.
    CPC .............. *A61M2005/1403* (2013.01); *A61M 2202/0021* (2013.01); *A61M 2202/0413* (2013.01); *A61M 2205/07* (2013.01); *A61M 2205/3331* (2013.01); *A61M 2205/3375* (2013.01); *A61M 2205/3389* (2013.01); *A61M 2205/3393* (2013.01)

(56) References Cited

U.S. PATENT DOCUMENTS

| | | | |
|---|---|---|---|
| 1,505,050 | A | 8/1924 | Lauritsen |
| 2,292,007 | A | 8/1942 | Morgan |
| 3,044,236 | A | 7/1962 | Bearden et al. |
| 3,074,645 | A | 1/1963 | Main |
| 3,095,062 | A | 6/1963 | Neely |
| 3,229,445 | A | 1/1966 | Kraft |
| 3,287,885 | A | 11/1966 | Sommer |
| 3,295,297 | A | 1/1967 | Collins |
| 3,342,019 | A | 9/1967 | Smythe |
| 3,412,760 | A | 11/1968 | Franck |
| 3,527,572 | A | 9/1970 | Urkiewicz |
| 3,581,464 | A | 6/1971 | Bhuta et al. |
| 3,598,727 | A | 8/1971 | Wilock |
| 3,677,710 | A | 7/1972 | Hirsch |
| 3,744,492 | A | 7/1973 | Leibinsohn |
| 3,756,234 | A | 9/1973 | Kopp |
| 3,769,207 | A | 10/1973 | Baer |
| 3,771,288 | A | 11/1973 | Wisman et al. |
| 3,795,088 | A | 3/1974 | Esmond |
| 3,827,561 | A | 8/1974 | Serfass et al. |
| 3,830,234 | A | 8/1974 | Kopp |
| 3,834,386 | A | 9/1974 | Sisley |
| 3,849,071 | A | 11/1974 | Kayser |
| 3,908,653 | A | 9/1975 | Kettering |
| 3,964,479 | A | 6/1976 | Boag et al. |
| 3,976,311 | A | 8/1976 | Spendlove |
| 3,985,134 | A | 10/1976 | Lissot et al. |
| 3,996,027 | A | 12/1976 | Schnell et al. |
| 4,031,891 | A | 6/1977 | Jess |
| 4,038,190 | A | 7/1977 | Baudet et al. |
| 4,047,563 | A | 9/1977 | Kurata |
| 4,048,995 | A | 9/1977 | Mittleman |
| 4,054,522 | A | 10/1977 | Pinkerton |
| 4,061,031 | A | 12/1977 | Grimsrud |
| 4,102,655 | A | 7/1978 | Jeffery et al. |
| 4,137,160 | A | 1/1979 | Ebling et al. |
| 4,149,860 | A | 4/1979 | Kulik |
| 4,151,088 | A | 4/1979 | Wolf, Jr. et al. |
| 4,191,182 | A | 3/1980 | Popovich et al. |
| 4,200,095 | A | 4/1980 | Reti |
| 4,293,413 | A | 10/1981 | Schnell |
| 4,304,670 | A | 12/1981 | Watanabe et al. |
| 4,311,137 | A | 1/1982 | Gerard |
| 4,325,715 | A | 4/1982 | Bowman et al. |
| 4,332,264 | A | 6/1982 | Gortz |
| 4,344,777 | A | 8/1982 | Siposs |
| 4,345,919 | A | 8/1982 | Wilkinson et al. |
| 4,345,999 | A | 8/1982 | Sigdell et al. |
| 4,353,368 | A | 10/1982 | Slovak et al. |
| 4,363,641 | A | 12/1982 | Finn, III |
| 4,368,118 | A | 1/1983 | Siposs |
| 4,427,009 | A | 1/1984 | Wells et al. |
| 4,433,971 | A | 2/1984 | Lindsay et al. |
| 4,464,172 | A | 8/1984 | Lichtenstein |
| 4,486,188 | A | 12/1984 | Altshuler et al. |
| 4,493,705 | A | 1/1985 | Gordon et al. |
| 4,512,163 | A | 4/1985 | Wells et al. |
| 4,531,937 | A | 7/1985 | Yates |
| 4,568,333 | A | 2/1986 | Sawyer et al. |
| 4,583,981 | A | 4/1986 | Urquhart et al. |
| 4,586,925 | A | 5/1986 | Carlsson et al. |
| 4,622,032 | A | 11/1986 | Katsura et al. |
| 4,643,713 | A | 2/1987 | Viitala |
| 4,643,715 | A | 2/1987 | Isono et al. |
| 4,666,598 | A | 5/1987 | Heath et al. |
| 4,681,606 | A | 7/1987 | Swan, Jr. et al. |
| 4,722,725 | A | 2/1988 | Sawyer et al. |
| 4,722,731 | A | 2/1988 | Vailancourt |
| 4,734,269 | A | 3/1988 | Clarke et al. |
| 4,806,135 | A | 2/1989 | Siposs |
| 4,850,998 | A * | 7/1989 | Schoendorfer ..... A61M 1/3672 210/139 |
| 4,923,612 | A | 5/1990 | Trivett et al. |
| 4,932,987 | A | 6/1990 | Molina |
| 4,941,875 | A | 7/1990 | Brennan |
| 4,946,439 | A | 8/1990 | Eggers |
| D311,061 | S | 10/1990 | Vrana et al. |
| 4,976,685 | A | 12/1990 | Block, Jr. |
| 4,997,464 | A | 3/1991 | Kopf |
| 5,047,147 | A | 9/1991 | Chevallet et al. |
| 5,049,492 | A | 9/1991 | Sauer et al. |
| 5,059,173 | A | 10/1991 | Sacco |
| 5,061,236 | A | 10/1991 | Sutherland et al. |
| 5,061,365 | A | 10/1991 | Utterberg |
| 5,112,480 | A | 5/1992 | Hukasawa |
| 5,167,921 | A | 12/1992 | Gordon |
| 5,178,763 | A | 1/1993 | Delaunay |
| 5,194,145 | A | 3/1993 | Schoendorfer |
| 5,204,000 | A | 4/1993 | Steadman et al. |
| 5,228,889 | A | 7/1993 | Cortial et al. |
| 5,234,608 | A | 8/1993 | Duff |
| 5,246,560 | A | 9/1993 | Nekoksa et al. |
| 5,259,961 | A | 11/1993 | Eigendorf |
| 5,268,077 | A | 12/1993 | Bubik et al. |
| 5,328,461 | A | 7/1994 | Utterberg |
| 5,336,165 | A | 8/1994 | Twardowski |
| 5,356,376 | A | 10/1994 | Milijasevic et al. |
| 5,358,481 | A | 10/1994 | Todd et al. |
| 5,368,555 | A | 11/1994 | Sussman et al. |
| 5,394,732 | A | 3/1995 | Johnson et al. |
| 5,411,705 | A | 5/1995 | Thor et al. |
| 5,421,815 | A | 6/1995 | Noguchi et al. |
| 5,429,595 | A | 7/1995 | Wright, Jr. et al. |
| 5,441,636 | A | 8/1995 | Chevallet et al. |
| 5,468,388 | A | 11/1995 | Goddard et al. |
| 5,484,397 | A | 1/1996 | Twardowski |
| 5,489,385 | A | 2/1996 | Raabe et al. |
| 5,490,925 | A | 2/1996 | Eigendorf |
| 5,503,801 | A * | 4/1996 | Brugger ............. A61M 1/3627 210/436 |
| 5,509,895 | A | 4/1996 | Noguchi et al. |
| 5,520,640 | A | 5/1996 | Utterberg |
| 5,529,685 | A | 6/1996 | Irie et al. |
| 5,578,070 | A | 11/1996 | Utterberg |
| 5,591,251 | A | 1/1997 | Brugger |
| 5,605,540 | A | 2/1997 | Utterberg |
| 5,637,081 | A | 6/1997 | Noguchi et al. |
| 5,643,205 | A | 7/1997 | Utterberg |
| 5,650,071 | A | 7/1997 | Brugger et al. |
| 5,674,199 | A | 10/1997 | Brugger |
| 5,681,294 | A | 10/1997 | Osborne et al. |
| 5,683,355 | A | 11/1997 | Fini et al. |
| 5,690,831 | A | 11/1997 | Kenley et al. |
| 5,702,606 | A | 12/1997 | Peter, Jr. et al. |
| 5,713,865 | A | 2/1998 | Manning et al. |
| 5,725,776 | A | 3/1998 | Kenley et al. |
| 5,730,730 | A | 3/1998 | Darling, Jr. |
| 5,763,266 | A | 6/1998 | Palsson et al. |
| 5,776,091 | A | 7/1998 | Brugger et al. |
| 5,776,345 | A | 7/1998 | Truitt et al. |
| 5,800,597 | A | 9/1998 | Perrotta et al. |
| 5,830,185 | A | 11/1998 | Block, Jr. |
| 5,849,065 | A | 12/1998 | Wojke |
| 5,851,202 | A | 12/1998 | Carlsson |
| 5,858,239 | A | 1/1999 | Kenley et al. |
| 5,863,421 | A | 1/1999 | Peter, Jr. et al. |
| 5,895,368 | A | 4/1999 | Utterberg |

(56) References Cited

U.S. PATENT DOCUMENTS

| | | |
|---|---|---|
| 5,902,476 A | 5/1999 | Twardowski |
| 5,910,252 A | 6/1999 | Truitt et al. |
| 5,928,889 A | 7/1999 | Bakich et al. |
| 5,931,990 A | 8/1999 | Andrews |
| 5,932,103 A | 8/1999 | Kenley et al. |
| 5,948,251 A | 9/1999 | Brugger |
| 5,951,870 A | 9/1999 | Utterberg |
| 5,980,741 A | 11/1999 | Schnell et al. |
| 5,983,947 A | 11/1999 | Utterberg |
| 5,989,318 A | 11/1999 | Schroll |
| 6,010,623 A | 1/2000 | Schnell et al. |
| 6,019,824 A | 2/2000 | Schnell |
| 6,046,806 A | 4/2000 | Thompson |
| 6,051,134 A | 4/2000 | Schnell et al. |
| 6,053,967 A | 4/2000 | Heilmann et al. |
| 6,066,111 A | 5/2000 | Brockhoff |
| 6,071,269 A | 6/2000 | Schnell et al. |
| 6,117,342 A | 9/2000 | Schnell et al. |
| 6,132,616 A | 10/2000 | Twardowski et al. |
| 6,146,536 A | 11/2000 | Twardowski |
| 6,171,484 B1 | 1/2001 | Schnell et al. |
| 6,176,903 B1 | 1/2001 | Wamsiedler |
| 6,187,198 B1 | 2/2001 | Utterberg |
| 6,206,954 B1 | 3/2001 | Schnell et al. |
| 6,251,167 B1 | 6/2001 | Berson |
| 6,274,034 B1 | 8/2001 | Nikaido et al. |
| 6,302,860 B1 | 10/2001 | Gremel et al. |
| 6,312,414 B1 | 11/2001 | Brockhoff et al. |
| 6,331,252 B1 | 12/2001 | El Sayyid et al. |
| 6,344,139 B1 | 2/2002 | Utterberg |
| 6,357,600 B1 | 3/2002 | Scagliarini |
| 6,361,518 B1 | 3/2002 | Brierton et al. |
| 6,391,541 B1 | 5/2002 | Petersen et al. |
| 6,391,638 B1 | 5/2002 | Shaaltiel |
| 6,464,878 B2 | 10/2002 | Utterberg |
| 6,481,455 B2 | 11/2002 | Gustafson et al. |
| 6,491,656 B1 | 12/2002 | Morris |
| 6,514,255 B1 | 2/2003 | Ferree |
| 6,524,267 B1 | 2/2003 | Gremel et al. |
| 6,537,356 B1 | 3/2003 | Soriano |
| 6,551,513 B2 | 4/2003 | Nikaido et al. |
| 6,558,340 B1 | 5/2003 | Traeger |
| 6,561,997 B1 | 5/2003 | Funke et al. |
| 6,562,107 B2 | 5/2003 | Purdom et al. |
| 6,572,576 B2 | 6/2003 | Brugger et al. |
| 6,582,604 B2 | 6/2003 | Nikaido et al. |
| 6,595,948 B2 | 7/2003 | Suzuki et al. |
| 6,695,803 B1 | 2/2004 | Robinson et al. |
| 6,755,801 B2 | 6/2004 | Utterberg et al. |
| 6,827,862 B1 | 12/2004 | Brockhoff et al. |
| 6,830,553 B1 | 12/2004 | Burbank et al. |
| 6,918,887 B1 | 7/2005 | Gremel et al. |
| 7,004,924 B1 | 2/2006 | Brugger et al. |
| 7,040,142 B2 | 5/2006 | Burbank |
| 7,087,033 B2 | 8/2006 | Brugger et al. |
| 7,097,690 B2 | 8/2006 | Usher et al. |
| 7,169,352 B1 | 1/2007 | Felt et al. |
| 7,186,342 B2 | 3/2007 | Pirazzoli et al. |
| 7,189,352 B2 | 3/2007 | Carpenter et al. |
| 7,198,751 B2 | 4/2007 | Carpenter et al. |
| 7,204,958 B2 | 4/2007 | Olsen et al. |
| 7,214,312 B2 | 5/2007 | Brugger et al. |
| 7,335,334 B2 | 2/2008 | Olsen et al. |
| 7,540,958 B2 | 6/2009 | Chevallet et al. |
| 7,563,240 B2 | 7/2009 | Gross et al. |
| 7,566,315 B2 | 7/2009 | Hirabuki |
| 7,608,053 B2 | 10/2009 | Felt et al. |
| 7,651,474 B2 | 1/2010 | Van Waeg et al. |
| 7,682,563 B2 | 3/2010 | Carpenter et al. |
| 7,686,779 B1 | 3/2010 | Gibbs |
| 7,740,800 B2 | 6/2010 | Olsen et al. |
| 7,819,834 B2 | 10/2010 | Paul |
| 7,824,356 B2 | 11/2010 | Wieting et al. |
| 7,829,018 B2 | 11/2010 | Olsen et al. |
| 7,922,683 B2 | 4/2011 | Ogihara et al. |
| 8,057,419 B2 | 11/2011 | Ellingboe et al. |
| 8,105,258 B2 | 1/2012 | Lannoy |
| 8,211,049 B2 | 7/2012 | Min |
| 8,366,649 B2 | 2/2013 | Ibragimov |
| 8,444,587 B2 | 5/2013 | Kelly et al. |
| 8,480,606 B2 | 7/2013 | Wieting et al. |
| 8,545,754 B2 | 10/2013 | Carpenter et al. |
| 8,628,489 B2 | 1/2014 | Pages et al. |
| 8,647,289 B2 | 2/2014 | Pages et al. |
| 8,684,959 B2 | 4/2014 | Paolini et al. |
| 8,685,258 B2 | 4/2014 | Nguyen et al. |
| 8,702,637 B2 | 4/2014 | Pages et al. |
| 8,877,063 B2 | 11/2014 | Kawarabata et al. |
| 8,894,600 B2 | 11/2014 | Kelly et al. |
| 8,939,926 B2 | 1/2015 | Wieting et al. |
| 8,956,317 B2 | 2/2015 | Rada |
| 2001/0042441 A1 | 11/2001 | Purdom et al. |
| 2003/0009123 A1* | 1/2003 | Brugger ............... A61M 1/3626 604/4.01 |
| 2004/0019313 A1 | 1/2004 | Childers et al. |
| 2004/0069709 A1* | 4/2004 | Brugger ............... A61M 1/3462 210/646 |
| 2004/0167457 A1* | 8/2004 | Tonelli ................... A61M 1/16 604/6.09 |
| 2005/0118059 A1 | 6/2005 | Olsen et al. |
| 2005/0131332 A1 | 6/2005 | Kelly et al. |
| 2005/0230314 A1* | 10/2005 | Kim ....................... A61M 1/16 210/646 |
| 2005/0234384 A1 | 10/2005 | Westberg et al. |
| 2005/0261619 A1 | 11/2005 | Gay |
| 2006/0089586 A1 | 4/2006 | Kaus et al. |
| 2006/0213835 A1 | 9/2006 | Nimura et al. |
| 2008/0171960 A1* | 7/2008 | Brieske ............... A61M 1/1698 604/4.01 |
| 2009/0101550 A1 | 4/2009 | Muller et al. |
| 2010/0089837 A1 | 4/2010 | Inoue et al. |
| 2010/0160137 A1 | 6/2010 | Scibona et al. |
| 2010/0192686 A1* | 8/2010 | Kamen ................... A61M 1/16 73/290 R |
| 2011/0040229 A1 | 2/2011 | Hannan et al. |
| 2011/0137224 A1 | 6/2011 | Ibragimov |
| 2011/0163030 A1* | 7/2011 | Weaver ............... A61M 1/3627 210/637 |
| 2013/0248446 A1* | 9/2013 | Frugier ............... A61M 1/1656 210/638 |
| 2014/0100506 A1 | 4/2014 | Pages et al. |
| 2014/0138294 A1 | 5/2014 | Fulkerson et al. |
| 2014/0148750 A1 | 5/2014 | Pages et al. |
| 2014/0174997 A1 | 6/2014 | Nimura et al. |
| 2014/0217020 A1 | 8/2014 | Meyer et al. |
| 2014/0217027 A1 | 8/2014 | Meyer et al. |
| 2014/0276376 A1* | 9/2014 | Rohde ................... A61M 1/287 604/29 |
| 2015/0060362 A1 | 3/2015 | Pouchoulin |

FOREIGN PATENT DOCUMENTS

| | | |
|---|---|---|
| DE | 3442744 | 6/1986 |
| EP | 0 058 325 | 8/1982 |
| EP | 0 106 026 | 4/1984 |
| EP | 0 143 340 | 6/1985 |
| EP | 0 318 993 | 6/1989 |
| EP | 0 350 675 | 1/1990 |
| EP | 0 501 144 | 1/1992 |
| EP | 560368 A2 | 9/1993 |
| EP | 0 587 251 | 3/1994 |
| EP | 720856 A2 | 7/1996 |
| EP | 560368 B1 | 2/1998 |
| EP | 826383 A2 | 3/1998 |
| EP | 826384 A2 | 3/1998 |
| EP | 720856 B1 | 10/2001 |
| EP | 826384 B1 | 10/2001 |
| EP | 0 776 222 | 4/2003 |
| EP | 1323439 A2 | 7/2003 |
| EP | 1323439 A3 | 8/2003 |
| EP | 826383 B1 | 8/2004 |
| GB | 1 408 319 | 10/1975 |

(56) References Cited

FOREIGN PATENT DOCUMENTS

| GB | 2 061 755 | 5/1981 |
| GB | 2 212 739 | 8/1989 |
| GR | 3026703 | 7/1998 |
| WO | WO 9640330 A1 * | 12/1996 | ........ A61M 5/16809 |
| WO | WO 98/23353 | 6/1998 |
| WO | WO 2012/125457 A1 | 9/2012 |

* cited by examiner

AUTOMATIC PURGING OF AIR FROM A FLUID PROCESSING SYSTEM

BACKGROUND

1. Field of the Disclosure

The invention relates to fluid processing systems and methods. More particularly, the invention relates to systems and methods for detecting air in a fluid return line and automatically purging the air therefrom.

2. Description of Related Art

Various blood processing systems now make it possible to collect particular blood constituents, instead of whole blood, from a blood source such as, but not limited to, a container of previously collected blood or other living or non-living source. Typically, in such systems, whole blood is drawn from a blood source, a particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents (e.g., red cells, platelets, and plasma) through centrifugation, such as in the AMICUS® separator from Fenwal, Inc. of Lake Zurich, Ill., or other centrifugal separation devices, or a spinning membrane-type separator, such as the AUTOPHERESIS-C® and AURORA® devices from Fenwal, Inc.

In some of these systems, an air detector is provided for detecting the presence of air bubbles in fluid being returned to the blood source. Known systems typically include an alert and/or alarm system that is programmed to generate an alert and/or alarm when air is detected in a fluid return line, which causes the pumps of the system to stop operating and closes the clamps or valves of the system to prevent air from being injected into the blood source. The intervention of an operator is then required to remove the air from the fluid return line, such as by pressing a button to cause the air to be vented from the fluid return line and then pressing another button to restart the system after visually confirming that the air has been vented. However, human interaction may prolong the time that the system is paused or inoperative, especially if a single operator is overseeing the simultaneous operation of multiple systems. Accordingly, the need remains for a fluid processing system that can automatically purge air from a fluid return line without requiring human intervention.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid processing system is provided for processing fluid and returning processed fluid and/or replacement fluid to a fluid recipient. The fluid processing system is configured to cooperate with a fluid flow circuit, which includes a fluid recipient line for returning processed fluid and/or replacement fluid from a fluid processing chamber to a fluid recipient. The system includes a fluid recipient pump operable in a first direction to pump processed fluid and/or replacement fluid through the fluid recipient line toward the fluid recipient and in a second direction to pump processed fluid and/or replacement fluid through the fluid recipient line away from the fluid recipient. The system also includes an air detection assembly configured to monitor the contents of the fluid recipient line and produce an output indicative of the presence of air in the fluid recipient line flowing toward the fluid recipient. A controller of the system is programmed to automatically instruct the fluid recipient pump to operate in the second direction (upon receiving the output from the air detection assembly) to pump processed fluid and/or replacement fluid containing air through the fluid recipient line away from the fluid recipient at least until the air in the fluid recipient line is removed from the fluid recipient line.

In another aspect, the combination of a fluid processing system and a fluid flow circuit configured to cooperate with the fluid processing system are provided for processing fluid and returning processed fluid and/or replacement fluid to a fluid recipient. The fluid flow circuit includes a fluid processing chamber and a fluid recipient line for returning processed fluid and/or replacement fluid from the fluid processing chamber to a fluid recipient. The fluid processing system includes a fluid recipient pump operable in a first direction to pump processed fluid and/or replacement fluid through the fluid recipient line toward the fluid recipient and in a second direction to pump processed fluid and/or replacement fluid through the fluid recipient line away from the fluid recipient. The system also includes an air detection assembly configured to monitor the contents of the fluid recipient line and produce an output indicative of the presence of air in the fluid recipient line flowing toward the fluid recipient. A controller of the system is programmed to automatically instruct the fluid recipient pump to operate in the second direction (upon receiving the output from the air detection assembly) to pump processed fluid and/or replacement fluid containing air through the fluid recipient line away from the fluid recipient at least until the air in the fluid recipient line is removed from the fluid recipient line.

In yet another aspect, a method is provided for processing a fluid and returning processed fluid and/or replacement fluid to a fluid recipient. The method includes obtaining fluid from a fluid source and processing the fluid. Processed fluid and/or replacement fluid is pumped toward a fluid recipient, with the fluid being monitored to detect the presence of air. If air is detected in the processed fluid and/or replacement fluid being pumped toward the fluid recipient, then the processed fluid and/or replacement fluid containing air is automatically pumped away from the fluid recipient until the air has been removed from the processed fluid and/or replacement fluid.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
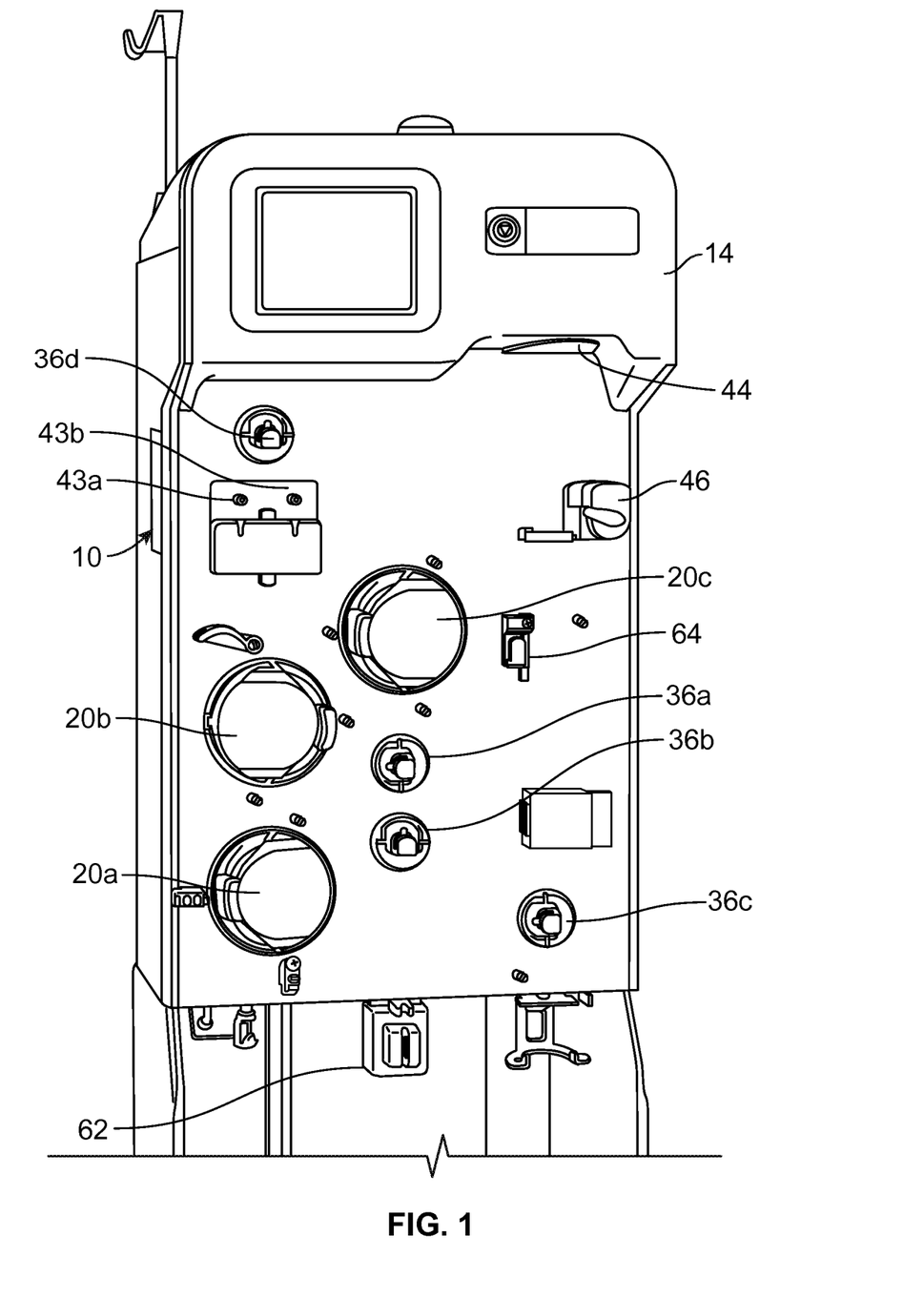
FIG. 1 is a front perspective view of an exemplary fluid processing system according to an aspect of the present disclosure.
Figure 2:
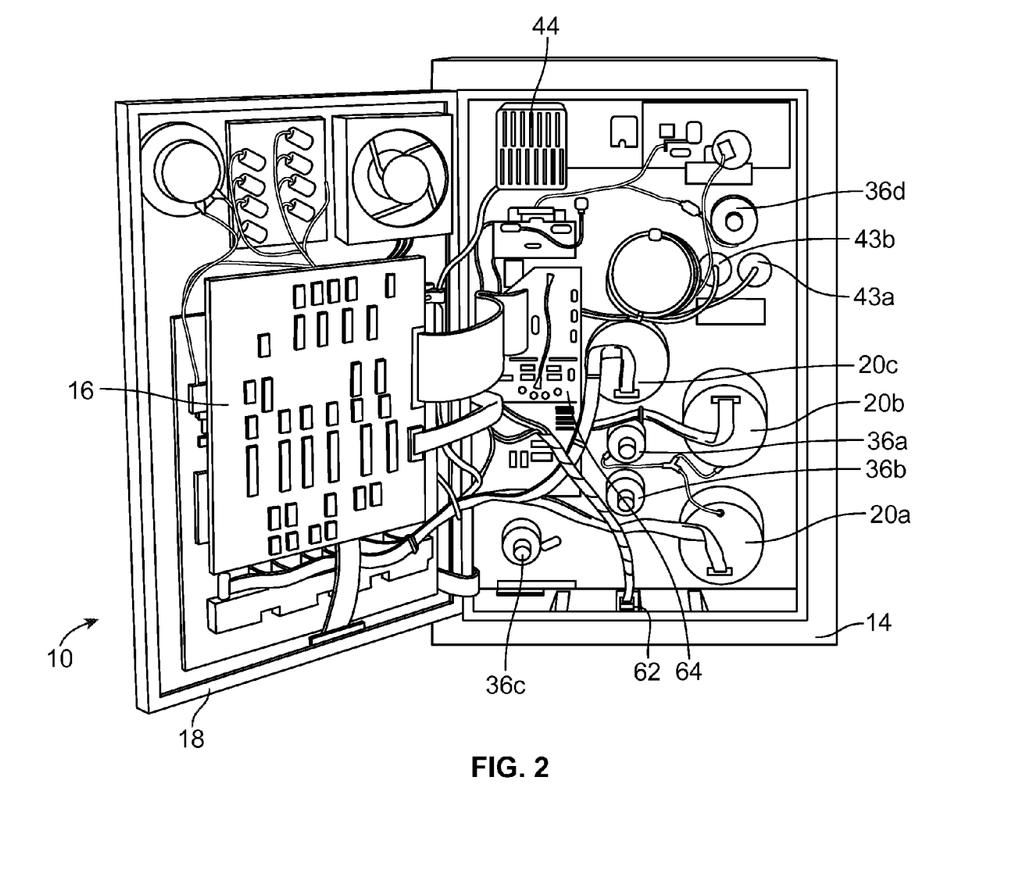
FIG. 2 is a rear perspective view of the fluid processing system of FIG. 1, with a rear door thereof in an open position.
Figure 3:
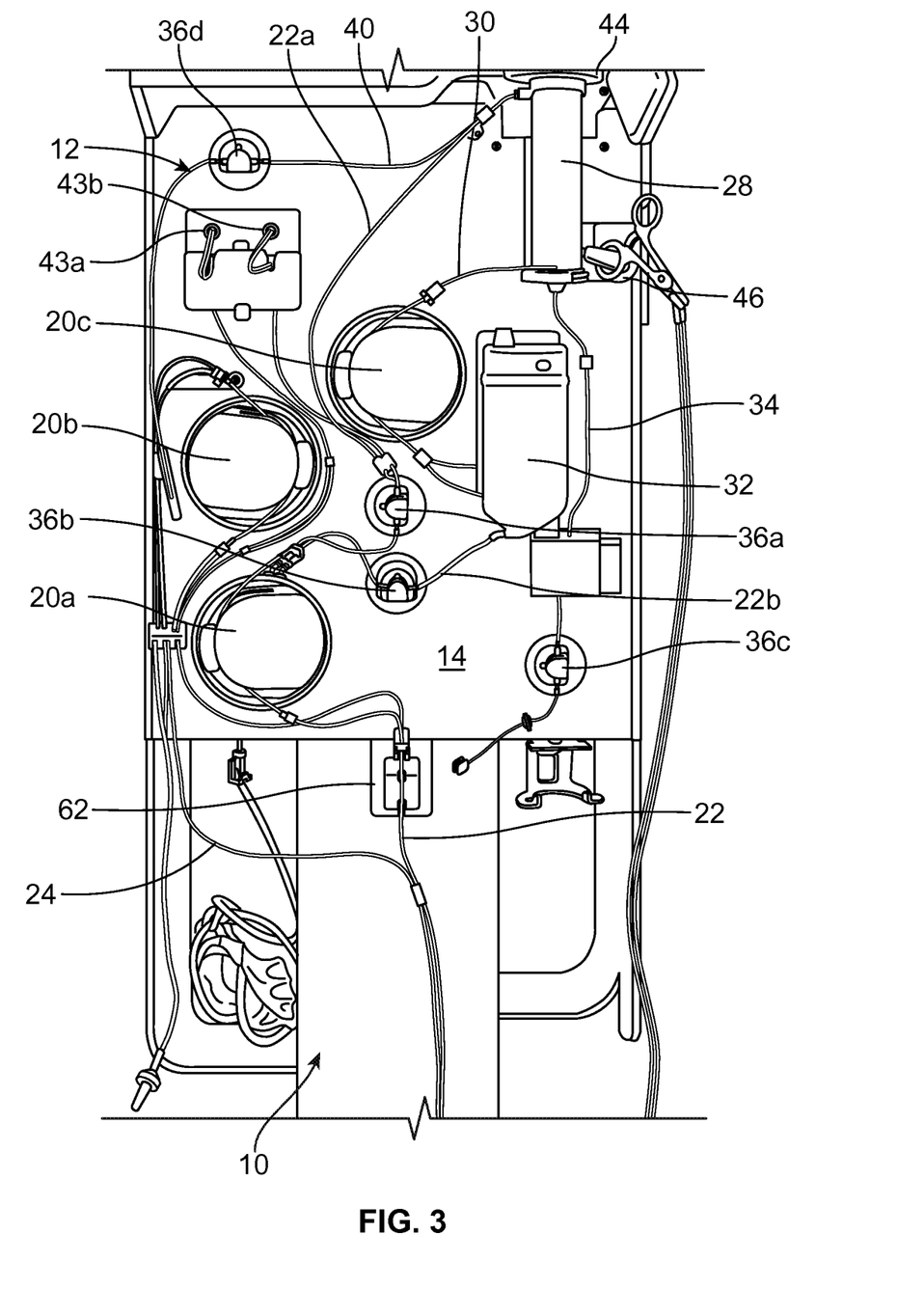
FIG. 3 is a front perspective view of the fluid processing system of FIG. 1, with a fluid flow circuit associated therewith.

According to an aspect of the present disclosure, a durable or reusable fluid processing system is used in combination with a separate fluid flow circuit (which may be disposable) to process a fluid from a fluid source, such as by separating the fluid into two or more constituent parts (as will be described in greater detail herein) or infusing an additive into the fluid or otherwise treating the fluid (e.g., by employing a photo-inactivation step). FIGS. 1 and 2 illustrate an exemplary fluid processing system 10, while FIG. 3 illustrates an exemplary fluid flow circuit 12 mounted onto the fluid processing system 10, but it should be understood that the illustrated fluid processing system 10 and fluid flow circuit 12 are merely exemplary of such systems and circuits and that differently configured fluid processing systems and fluid flow circuits may be provided without departing from the scope of the present disclosure.

The system 10 of FIG. 1 is configured for separating whole blood, but it may be used with any fluid to be processed and then at least partially returned to a fluid source or other recipient. The fluid may come from any fluid source and be returned to any recipient, which may be the same as or different from the fluid source. In one embodiment, the fluid source/recipient is a living donor or patient (e.g., a human blood donor), while in other embodiments the fluid source and/or fluid recipient may be a non-living source/recipient (e.g., a blood bag or fluid container).

Figure 5:
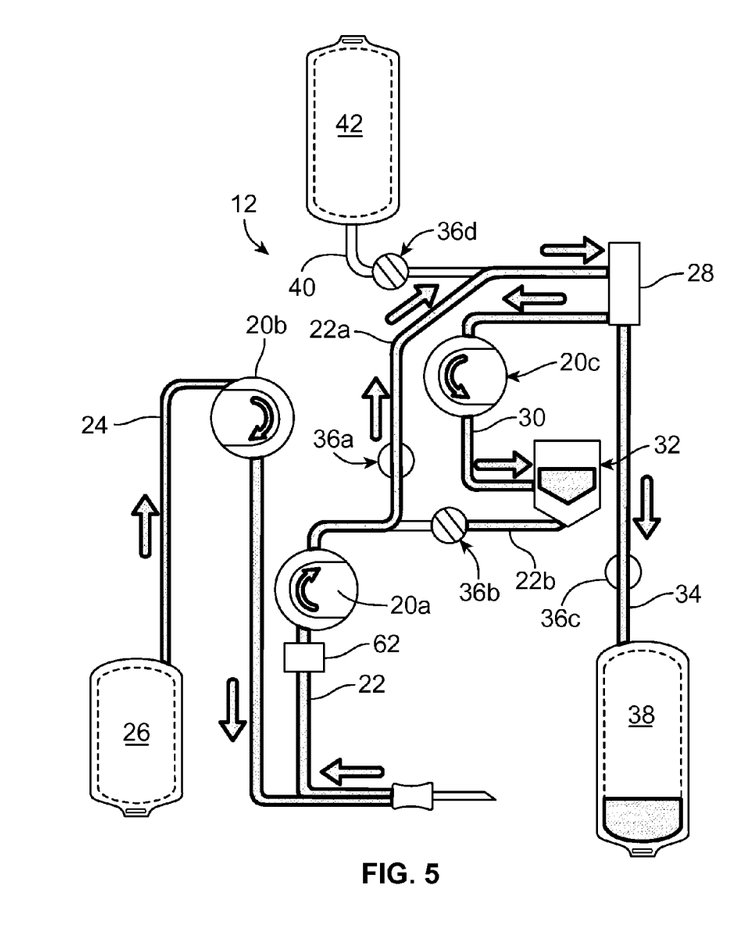
FIG. 5 is a schematic view of the fluid flow circuit and fluid processing system of FIG. 3, in a fluid draw mode.
Figure 6:
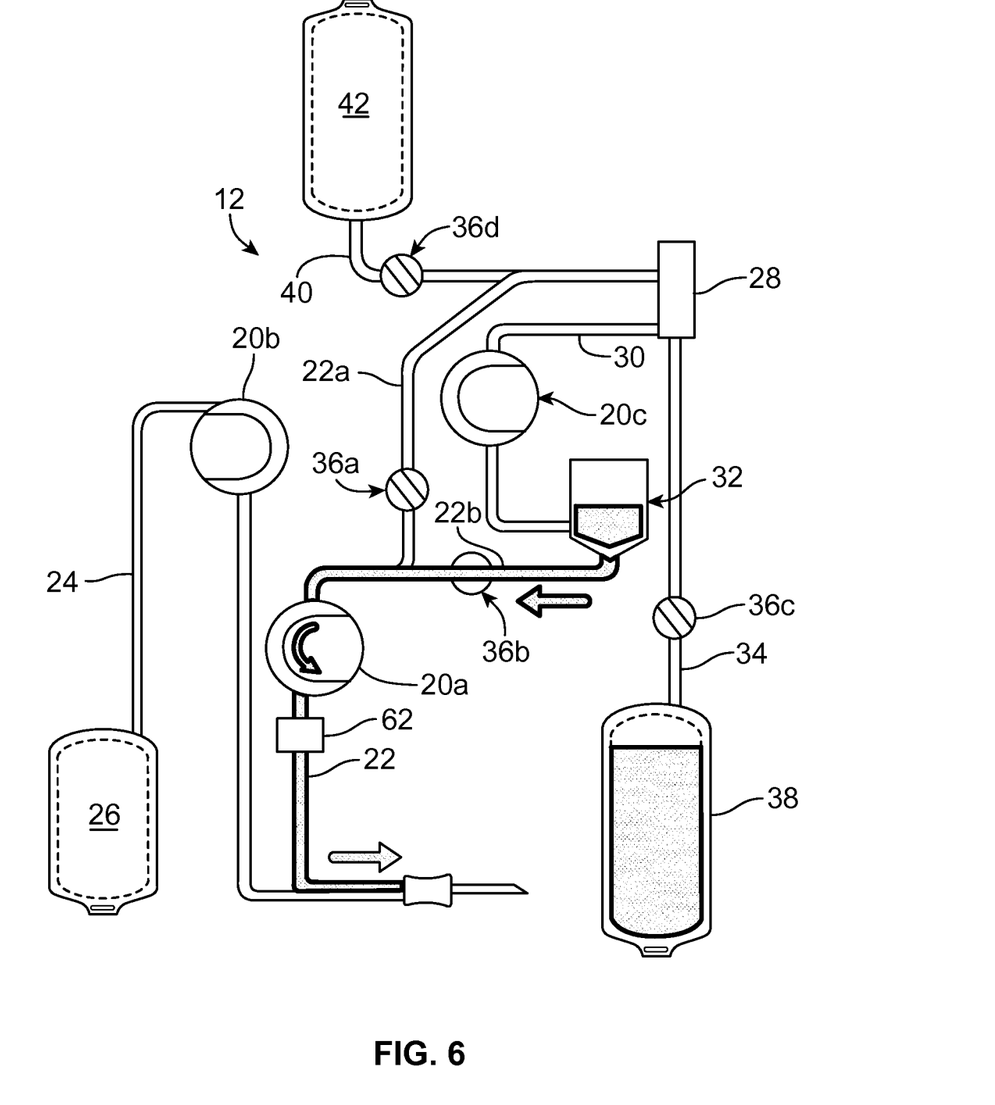
FIG. 6 is a schematic view of the fluid flow circuit and fluid processing system of FIG. 3, in a fluid return mode.

The illustrated system 10 includes a cabinet or housing 14, with several components positioned outside of the cabinet 14 (e.g., associated with a front wall or surface or panel of the cabinet 14) and additional components (including a central processing unit or controller 16) and interconnects positioned inside of the cabinet 14, which may be accessed by opening a rear door 18 of the system 10, as shown in FIG. 2. Among the system components positioned on the outside of the cabinet 14, one or more pumps or pump stations 20a-20c may be provided, with the pumps 20a-20c configured to accommodate tubing lines of the fluid flow circuit 12. One of the pumps 20a may be provided as a source/recipient access pump or fluid recipient pump, which may be associated with a source/recipient access line or fluid recipient line 22 of the fluid flow circuit 12 and operates to draw fluid from a fluid source (FIG. 5) and to return fluid to a fluid recipient (FIG. 6). Another one of the pumps 20b may be provided as an anticoagulant pump, which may be associated with an anticoagulant line 24 of the fluid flow circuit 12 and operates to add anticoagulant from an anticoagulant source or container 26 of the fluid flow circuit 12 (FIG. 5) to fluid drawn from the fluid source in the source/recipient access line 22 before the fluid enters into a fluid processing or separation module or chamber 28 of the fluid flow circuit 12. A third pump 20c may be provided as a return fluid pump or processed fluid pump, which may be associated with a return fluid outlet line 30 and operates to draw a return fluid (i.e., a fluid constituent to be returned to a fluid recipient) from the fluid separation chamber 28 and direct it into a return fluid reservoir or processed fluid reservoir 32 after the fluid has been separated into a return fluid and a collection fluid in the fluid separation chamber 28.

In the illustrated embodiment, the pumps 20a-20c are rotatable peristaltic pumps, but it is within the scope of the present disclosure for differently configured pumps, such as diaphragm or other pumps, to be provided. Furthermore, additional or alternative pumps may be provided without departing from the scope of the present disclosure. For example, a pump may be associated with a collection fluid outlet line 34 of the fluid flow circuit 12 to draw a collection fluid from the fluid separation chamber 28 after the fluid from the fluid source has been separated into a return fluid and a collection fluid. Also, as will be described in greater detail herein, the illustrated embodiment employs a single fluid flow tubing or flow path for both drawing fluid from a source and flowing or returning it to a recipient, which are carried out intermittently. The system 10 could employ separate draw and return flow paths or tubes without departing from the scope of the present disclosure.

In addition to the pumps 20a-20c, the external components of the system 10 may include one or more clamps or valves 36a-36d associated with the tubing lines of the fluid flow circuit 12. The clamps or valves 36a-36d may be variously configured and operate to selectively allow and prevent fluid flow through the associated tubing line. In the illustrated embodiment, one clamp or valve 36a may be provided as a fluid source/recipient clamp, which may be associated with a draw branch 22a of the source/recipient access line 22 of the fluid flow circuit 12 to allow (FIG. 5) or prevent (FIG. 6) the flow of fluid through the draw branch 22a of the source/recipient access line 22. Another one of the clamps or valves 36b may be provided as a reinfusion clamp or valve, which may be associated with a reinfusion branch 22b of the source/recipient access line 22 downstream of the return fluid reservoir 32 of the fluid flow circuit 12 to allow (FIG. 6) or prevent (FIG. 5) the flow of return fluid through the reinfusion branch 22b. A third clamp or valve 36c may be provided as a collection fluid clamp or valve, which may be associated with the collection fluid outlet line 34 to allow (FIG. 5) or prevent (FIG. 6) the flow of collection fluid through the collected outlet line 34 and into a collection fluid container 38. A fourth clamp or valve 36d may be provided as a replacement fluid clamp or valve, which may be associated with a replacement fluid line 40 of the fluid flow circuit 12 to allow or prevent the flow of a replacement fluid out of a replacement fluid source 42 (e.g., a bag or container at least partially filled with saline). Additional or alternative clamps or valves may also be provided without departing from the scope of the present disclosure.

The illustrated system 10 further includes one or more pressure sensors 43a and 43b that may be associated with the fluid flow circuit 12 to monitor the pressure within one or more of the tubing lines of the fluid flow circuit 12 during operation of the pumps 20a-20c and clamps or valves 36a-36d. In one embodiment, one pressure sensor 43a may be associated with a tubing line that draws fluid from a fluid source and/or directs processed fluid to a fluid recipient, while the other pressure sensor 43b may be associated with a tubing line that directs fluid into or out of the fluid separation chamber 28 to assess the pressure within the fluid separation chamber 28, but the pressure sensors 43a and 43b may also be associated with other tubing lines without departing from the scope of the present disclosure. The pressure sensors 43a and 43b may send signals to the system controller 16 that are indicative of the pressure within the tubing line or lines being monitored by the pressure sensor 43a, 43b. If the controller 16 determines that an improper pressure is present within the fluid flow circuit 12 (e.g., a high pressure due to an occlusion of one of the tubing lines), then the controller 16 may instruct one or more of the pumps 20a-20c and/or one or more of the clamps or valves 36a-36d to act so as to alleviate the improper pressure condition (e.g., by reversing the direction of operation of one of the pumps 20a-20c and/or opening or closing one of the clamps or valves 36a-36d). Additional or alternative pressure sensors may also be provided without departing from the scope of the present disclosure.

The system 10 may also include a separation actuator or processing actuator 44 that interacts with a portion of the fluid separation chamber 28 to operate the fluid separation chamber 28. A chamber lock 46 may also be provided to hold the fluid separation chamber 28 in place with respect to the system cabinet 14 and in engagement with the separation actuator 44. The configuration and operation of the separation actuator 44 depends upon the configuration of the fluid separation chamber 28. In the illustrated embodiment, the fluid separation chamber 28 is provided as a spinning membrane-type separator, such as a separator of the type described in greater detail in U.S. Pat. Nos. 5,194,145 and 5,234,608 or in PCT Patent Application Publication No. WO 2012/125457 A1, all of which are hereby incorporated herein by reference. If provided as a spinning membrane-type separator, the fluid separation chamber 28 may include a tubular housing 48 (FIG. 4), with a microporous membrane 50 positioned therein. An inlet 52 allows a fluid from a fluid source to enter into the housing 48 (via the draw branch 22a of the source/recipient access line 22), while a side outlet 54 allows return fluid to exit the housing 48 (via the return fluid outlet line 30) and a bottom outlet 56 allows collection fluid to exit the housing 48 (via the collection fluid outlet line 34) after the fluid from the fluid source has been separated into return fluid and collection fluid.

Figure 4:
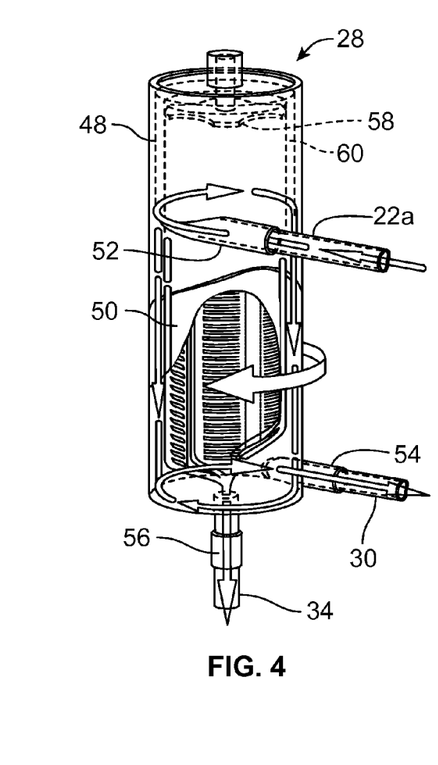
FIG. 4 is a front perspective view of a fluid separation chamber of the fluid flow circuit of FIG. 3, with a portion thereof broken away for illustrative purposes.

In the illustrated embodiment, the separation actuator 44 is provided as a driver that is magnetically coupled to a rotor 58 on which the membrane 50 is mounted, with the separation actuator 44 causing the rotor 58 and membrane 50 to rotate about the central axis of the housing 48. The rotating rotor 58 and membrane 50 create Taylor vortices within a gap 60 between the housing 48 and the membrane 50, which tend to transport the return fluid away from the membrane 50 to exit the fluid separation chamber 28 via the side outlet 54, while the collection fluid passes through the membrane 50 toward the central axis of the housing 48 to exit the fluid separation chamber 28 via the bottom outlet 56. In one embodiment, whole blood from a blood source is separated into cellular blood components (return fluid) and substantially cell-free plasma (collection fluid). It should be understood that the present disclosure is not limited to a particular fluid processing chamber or device and that the illustrated and described chamber 28, which separates the fluid into two constituents, is merely exemplary. For example, in other embodiments, a centrifugal device that separates fluid components based on density, rather than size, may be employed instead of a spinning membrane-type fluid separation chamber, or a processing device that treats the fluid without separating it (e.g., a photo-inactivation chamber) may be incorporated into the fluid flow circuit 12 without departing from the scope of the present disclosure.

According to one method of using the illustrated fluid processing system 10 and fluid flow circuit 12, a fluid is drawn from a fluid source into the fluid separation chamber 28 during a draw phase or mode (FIG. 5), where it separated into return fluid and collection fluid. The collection fluid is retained by the system 10, while the return fluid is returned to the fluid source during a return or reinfusion phase or mode (FIG. 6). In one embodiment, the draw and return phases are repeatedly alternated (drawing from the fluid source, separating the fluid from the fluid source into return fluid and collection fluid, and then pumping the collection fluid to the fluid source or a different recipient) until a target (e.g., a particular amount of collection fluid) is achieved. All of the draw phases and all of the return phases may be identical or may differ from each other. For example, a final draw phase may draw less fluid from the fluid source than the previous draw phases and a final return phase may infuse a combination of return fluid and replacement fluid to the fluid recipient, whereas the previous return phases pump only return fluid to the fluid recipient.

Figure 7:
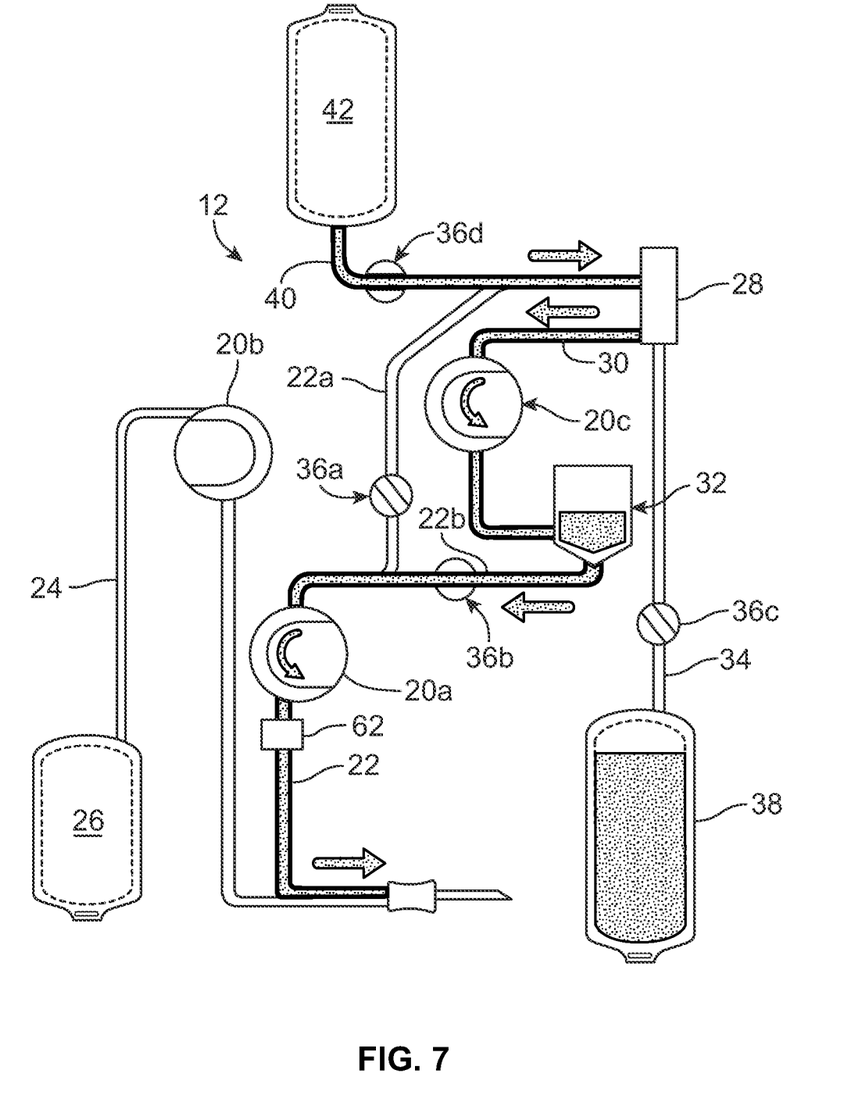
FIG. 7 is a schematic view of the fluid flow circuit and fluid processing system of FIG. 3, in a replacement fluid return mode.

FIG. 7 shows an exemplary phase or mode in which replacement fluid (e.g., saline) is directed to the fluid recipient, either alone or with an amount of return/processed fluid. In the phase of FIG. 7, the clamp or valve 36d associated with the replacement fluid line 40 is opened to allow replacement fluid to flow out of the replacement fluid source 42. The clamp or valve 36a associated with the draw branch 22a of the source/recipient access line 22 may be in a closed condition to prevent fluid flow therethrough, such that the replacement fluid is directed into the fluid separation chamber 28. The replacement fluid is pulled out of the fluid separation chamber 28 and into the return fluid reservoir 32 by operation of the pump 20c associated with the return fluid outlet line 30. If there is any return fluid in the return fluid reservoir 32, then the replacement fluid mixes with the return fluid prior to being pumped to the fluid recipient by the pump 20a associated with the fluid recipient line 22, otherwise the replacement fluid alone may be pumped to the fluid recipient. In one embodiment, the replacement fluid return mode of FIG. 7 is carried out only once, as a final return phase (e.g., when the amount of return fluid in the return fluid reservoir 32 is at a sufficiently low level) in which a mixture of return fluid and replacement fluid is returned to the fluid recipient. This may be advantageous to ensure that all of the return fluid in the return fluid reservoir 32 (along with any remaining in the fluid separation chamber 28) is rinsed out of the return fluid reservoir 32 and pumped to the fluid recipient.

In other embodiments, the replacement fluid return mode of FIG. 7 may be carried out at other times, such as earlier in the procedure, at multiple scheduled times during a procedure, and/or at any time upon a request from the operator and/or using a different path between the replacement fluid source 42 and the fluid recipient. For example, it may be advantageous for the replacement fluid to bypass the fluid separation chamber 28 and the return fluid reservoir 32 if the replacement fluid is being pumped to a fluid recipient earlier in the procedure. In this case, the clamp or valve 36d associated with the replacement fluid line 40 and the clamp or valve 36a associated with the draw branch 22a of the source/recipient access line 22 may be opened to allow fluid flow therethrough, with the clamp or valve 36b associated with the reinfusion branch 22b in a closed condition to prevent fluid flow therethrough. The pump 20a associated with the fluid recipient line 22 may be activated (with the other two pumps 20b and 20c inactive) to draw replacement fluid out of the replacement fluid source 42 and through the replacement fluid line 40, the draw branch 22a, and finally the source/recipient access line 22 to the fluid recipient.

The processed or return fluid and/or replacement fluid being returned to the fluid recipient may be monitored to detect the presence of air. Detection of air in a fluid return line of a fluid processing system (e.g., an apheresis system or a dialysis system) is known, and any suitable air detection assembly may be incorporated into fluid processing systems according to the present disclosure. In the illustrated embodiment, an air detection assembly 62 of the fluid processing system 10 is part of the front panel of the cabinet 14, and configured to receive a portion of the reinfusion branch 22b of the fluid recipient line 22. The illustrated air detection assembly 62 is positioned downstream of the fluid recipient pump 20a (i.e., between the fluid recipient pump 20a and the fluid recipient), with the fluid recipient pump 20a being positioned between the processed fluid reservoir 32 and the air detection assembly 62 when the fluid flow circuit 12 has been mounted onto the fluid processing system 10.

In one embodiment, the air detection assembly 62 may be provided as an ultrasonic monitoring device, with at least one sound wave emitter and at least one sound wave receiver positioned on opposite sides of the fluid recipient line 22. An ultrasonic sound wave will travel through fluid (e.g., return fluid and/or replacement fluid) substantially unimpeded, whereas an ultrasonic sound wave traveling through an air bubble will arrive at the receiver with a reduced magnitude. The air detection assembly 62 may be associated with the system controller 16, which may issue instructions to the air detection assembly 62 (e.g., instructing the sound wave emitter and receiver when to be operative) and receive signals or outputs generated by the air detection assembly 62 (e.g., receiving an output of the sound wave receiver that is indicative of the contents of the reinfusion branch 22b of the fluid recipient line 22 passing through the air detection assembly 62). If the controller 16 receives an output from the sound wave receiver that is indicative of a low magnitude sound wave, then the controller may interpret the output as signifying the presence of air in the fluid recipient line 22. In other embodiments, other air detection assembly configurations (e.g., an optical monitor) and/or methods for detecting air in the fluid recipient line 22 may be employed without departing from the scope of the present disclosure.

If the air detection assembly 62 detects air in the fluid recipient line 22 moving toward the fluid recipient (e.g., in the return phase of FIG. 6 or the replacement fluid return phase of FIG. 7), then the controller 16 may automatically take steps to remove the air from the fluid recipient line 22. For example, in one embodiment, the controller 16 is programmed to pause or stop the operation of the fluid recipient pump 20a when air is detected in the fluid recipient line 22 moving toward the fluid recipient. If any of the other pumps 20b, 20c are operating, then the controller 16 may either pause operation of them as well or allow them to continue operating, either as before or in a modified capacity. The controller 16 may also generate an alert or an alarm to notify an operator that air is in the fluid recipient line 22 and that the system 10 is taking automated steps to remove the air from the fluid recipient line 22.

The controller 16 may then automatically instruct the fluid recipient pump 20a to operate in a second or reverse direction to move processed fluid and/or replacement fluid in the fluid recipient line 22 in a direction away from the fluid recipient to prevent air from being infused into the fluid recipient, which may be harmful if the fluid recipient is a living recipient (e.g., a human). The air detection assembly 62 may continue monitoring the processed fluid and/or replacement fluid in the fluid recipient line 22 as the fluid recipient pump 20a operates in the reverse direction to allow the controller 16 to confirm or verify that the air in the fluid recipient line 22 has been passed through the air detection assembly 62 away from the fluid recipient.

The fluid recipient pump 20a continues operating in the reverse or second direction until the air in the fluid recipient line 22 has been removed from the fluid recipient line 22. The location at which the air is removed from the fluid recipient line 22 may vary without departing from the scope of the present disclosure. For example, in the illustrated embodiment, the processed fluid and/or replacement fluid in the fluid recipient line 22 may be pumped into the processed fluid reservoir 32 at least until the air in the fluid recipient line 22 enters the processed fluid reservoir 32. The processed fluid reservoir 32 may be a flexible, expandable bag or container, such that air in the processed fluid reservoir 32 separates from the processed fluid and/or replacement fluid and partially inflates the processed fluid reservoir 32, effectively removing the air from the fluid recipient line 22. In other embodiments, the processed fluid and/or replacement fluid may be pumped to a different location (e.g., through a dedicated air vent line) to remove the air from the fluid recipient line 22. It may be advantageous for the fluid recipient pump 20a to operate beyond the point that the air in the fluid recipient line 22 has been removed therefrom, by pumping additional processed fluid to the air-removal location. By operating beyond the point that the air in the fluid recipient line 22 has been removed, the system 10 may better ensure that the air has been removed.

The controller 16 may determine when air has been removed from the fluid recipient line 22 in any suitable manner. For example, in one embodiment, the controller 16 may determine the amount of processed fluid and/or replacement fluid in the fluid recipient line 22 between the air and the processed fluid reservoir 32, which depends on the length of the fluid recipient line 22 between the air detection assembly 62 and the processed fluid reservoir 32. This may be advantageous if the length of the fluid recipient line 22 between the air detection assembly 62 and the processed fluid reservoir 32 is known, such as if a portion of the fluid recipient line 22 is particularly configured to be received within the air detection assembly 62 (e.g., by including a fixture that is pressed into the air detection assembly 62). When the fluid recipient pump 20a has been operated at least long enough to have moved that amount of processed fluid and/or replacement fluid in the reverse direction, the air will have been moved into the processed fluid reservoir 32, effectively removing the air from the fluid recipient line 22. As described above, the controller 16 may instruct the fluid recipient pump 20a to pump an additional amount of processed fluid and/or replacement fluid into the processed fluid reservoir 32 to ensure that the air has been removed from the fluid recipient line 22.

In some embodiments, the length of the fluid recipient line 22 between the processed fluid reservoir 32 and the air detection assembly 62 may vary, which may be the case if any portion of the fluid recipient line 22 may be received by the air detection assembly 62, rather than having a designated portion of the fluid recipient line 22 positioned within the air detection assembly 62. In this case, the controller 16 may be programmed to operate the fluid recipient pump 20a a predetermined or preselected amount of time or to a predetermined or preselected extent to ensure that the air has been removed from the fluid recipient line 22. For example, if the fluid recipient pump 20a is a rotatable peristaltic pump, the controller 16 may be programmed to instruct the fluid recipient pump 20a to operate in the reverse or second direction a preselected or predetermined number of rotations to ensure that the air in the fluid recipient line 22 has been pumped into the processed fluid reservoir 32.

It may be advantageous for the system 10 to include a separate mechanism to verify that air has been removed from the fluid recipient line 22 as a safety measure. For example, in the illustrated embodiment, the system 10 includes a processed fluid weigh scale 64 (FIGS. 1 and 2) associated with the processed fluid reservoir 32. The processed fluid weigh scale 64 may weigh the processed fluid reservoir 32 and the processed fluid and/or replacement fluid contained therein. In one embodiment, the controller 16 monitors the output of the processed fluid weigh scale 64 to determine that a sufficient amount of processed fluid and/or replacement fluid has been pumped back into the processed fluid reservoir 32 by the fluid recipient pump 20a so as to clear the air from the fluid recipient line 22. When the controller 16 has verified that the air has been removed from the fluid recipient line 22 (by reference to one or more readings from the processed fluid weigh scale 64), the controller 16 may instruct the fluid recipient pump 20a to operate in the first or forward direction to move fluid through the fluid recipient line 22 toward and to the fluid recipient.

In one embodiment, the controller 16 may continuously or periodically monitor and record the weight registered by the processed fluid weigh scale 64, such that the controller 16 is aware of the weight of the processed fluid reservoir 32 and the processed fluid and/or replacement fluid therein at different times throughout the course of a procedure. When the controller 16 determines that the fluid recipient pump 20a has pumped the air in the fluid recipient line 22 into the processed fluid reservoir 32, it may pause operation of the fluid recipient pump 20a. The controller 16 may compare the weight registered by the processed fluid weigh scale 64 at this time (which may be referred to as the "post-detection weight") to the weight registered by the processed fluid weigh scale 64 at a time before the air detection assembly 62 detected air in the fluid recipient line 22 (which may be referred to as the "pre-detection weight"). If the post-detection weight is sufficiently greater than the pre-detection weight, then the controller 16 will have verified that enough processed fluid and/or replacement fluid has been pumped back into the processed fluid reservoir 32 to remove the air from the fluid recipient line 22.

The difference in the pre- and post-detection weight that is required for the controller 16 to verify purgation of the air may vary without departing from the scope of the present disclosure. In one embodiment, there may be a short delay between the time at which air is detected and the time that the operation of the fluid recipient pump 20a can be paused. The amount of fluid pumped through the fluid recipient line 22 by the fluid recipient pump 20a during this response time may be referred to as the "post-detection amount" of fluid. In this embodiment, it may be advantageous for the required weight difference to be based at least in part on this "post-detection amount" of fluid. Preferably, the weight difference that is required for the controller 16 to verify purgation of air is at least equal to the sum of the weight of the fluid between the processed fluid reservoir 32 and the air detection assembly 62 plus the weight of the "post-detection amount" of fluid, which sum is equal to the weight of the fluid between the processed fluid reservoir 32 and the air bubble. It may be preferred to return an additional amount of fluid to the processed fluid reservoir 32 to ensure that the air has been pumped into the processed fluid reservoir 32.

The time used when selecting the pre-detection weight may vary without departing from the scope of the present disclosure. In the above example, the weight immediately before air is detected is treated as the pre-detection weight. In another embodiment, the controller 16 may determine the amount of time required for processed fluid and/or replacement fluid to be pumped from the processed fluid reservoir 32 to the air detection assembly 62, which may correspond to the amount of time required for the air to have been pumped from the processed fluid reservoir 32 to the air detection assembly 62. This amount of time is dependent on the length of the fluid recipient line 22 between the processed fluid reservoir 32 and the air detection assembly 62 and the volumetric flow rate of the processed fluid and/or replacement fluid through the fluid recipient line 22, which the controller 16 may determine by monitoring the operation of the fluid recipient pump 20a. The controller 16 may count backwards from the time that the air was detected by the air detection assembly 62 to determine the time that the air may have entered the fluid recipient line 22 from the processed fluid reservoir 32. The weight registered by the processed fluid weigh scale 64 shortly before this time (e.g., one second earlier) may be used to select the pre-detection weight as a safety measure, to ensure that enough processed fluid and/or replacement fluid has been pumped to the processed fluid reservoir 32 to remove the air from the fluid recipient line 22. In yet another embodiment, the time selected for the pre-detection weight may be a standard amount of time (e.g., five seconds) before air was detected by the air detection assembly 62. In any embodiment, it may be advantageous for an additional amount of fluid to be returned to the processed fluid reservoir 32 to account for the aforementioned response time for the pump 20a to be paused and/or to provide a safety buffer that ensures that more than enough fluid has been pumped into the processed fluid reservoir 32 to purge the air bubble.

When the air has been removed from the fluid recipient line 22 (either by being pumped into the processed fluid reservoir 32 or to another suitable venting or air-removal location) and the controller 16 has confirmed the same, the controller 16 may instruct the fluid recipient pump 20a to operate in the first or forward direction to move fluid through the fluid recipient line 22 toward and to the fluid recipient. The controller 16 may also generate an alarm or alert to notify the operator that the air has been cleared from the fluid recipient line 22 and that the fluid return phase is being continued. By such an arrangement, air may be detected and subsequently cleared from the fluid recipient line 22 without requiring human intervention.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid processing system for processing fluid and returning processed fluid and/or a replacement fluid to a fluid recipient, the fluid processing system being configured to cooperate with a fluid flow circuit including a fluid recipient line for drawing fluid into the fluid flow circuit and returning processed fluid and/or a replacement fluid from a fluid processing chamber to a fluid recipient, the fluid processing system comprising:
   a fluid recipient pump operable in a first direction to pump processed fluid and/or a replacement fluid through the fluid recipient line toward the fluid recipient and in a second direction to pump processed fluid and/or a replacement fluid through the fluid recipient line away from the fluid recipient;
   an air detection assembly configured to monitor the contents of the fluid recipient line and produce an output indicative of the presence of air in the fluid recipient line flowing toward the fluid recipient; and
   a controller programmed to receive the output from the air detection assembly and, upon receiving said output, automatically instruct the fluid recipient pump to operate in the second direction to pump processed fluid and/or replacement fluid containing air through the fluid recipient line away from the fluid recipient at least until the air in the fluid recipient line is removed from the fluid recipient line.

2. The fluid processing system of claim 1, further comprising a processed fluid weigh scale configured to measure first and second weights of at least a portion of the fluid flow circuit and the processed fluid and/or replacement fluid therein, the first weight being measured during operation of the fluid processing system to return processed fluid and/or replacement fluid from the fluid processing chamber toward the fluid recipient and the second weight being measured when operation of the fluid recipient pump is paused, wherein the controller is further programmed to
   instruct the fluid recipient pump to pause operation in either the first direction or the second direction after the air in the fluid recipient line has been removed from the fluid recipient line,
   compare the first and second weights, and
   if the first and second weights are substantially the same or if the second weight is greater than the first weight, instruct the fluid recipient pump to operate in the first direction to pump processed fluid and/or replacement fluid through the fluid recipient line toward the fluid recipient.

3. The fluid processing system of claim 1, wherein the controller is further programmed to verify that the air in the fluid recipient line has passed through the air detection assembly away from the fluid recipient during operation of the fluid recipient pump in the second direction.

4. The fluid processing system of claim 1, wherein
   the fluid recipient pump is a rotatable peristaltic pump, and
   the controller is programmed to, upon receiving said output, automatically instruct the fluid recipient pump to operate in the second direction for a preselected number of rotations to remove air from the fluid recipient line.

5. A combination of a fluid processing system and a fluid flow circuit configured to cooperate with the fluid processing system to process fluid and return processed fluid and/or replacement fluid to a fluid recipient, the combination comprising
   a fluid flow circuit including a fluid processing chamber, a fluid recipient line for returning processed fluid and/or replacement fluid from the fluid processing chamber to a fluid recipient, a draw branch directly connected to the fluid recipient line, and a reinfusion branch directly connected to the fluid recipient line; and
   a fluid processing system including
      a fluid recipient pump operable in a first direction to pump processed fluid and/or replacement fluid through the reinfusion branch and the fluid recipient line toward the fluid recipient and in a second direction to pump unprocessed fluid through the fluid recipient line and the draw branch to the fluid processing chamber and to pump processed fluid and/or replacement fluid through the fluid recipient line and the reinfusion branch away from the fluid recipient,
      an air detection assembly configured to monitor the contents of the fluid recipient line and produce an output indicative of the presence of air in the fluid recipient line flowing toward the fluid recipient, and
      a controller programmed to receive the output from the air detection assembly and, upon receiving said output, automatically instruct the fluid recipient pump to operate in the second direction to pump processed fluid and/or replacement fluid containing air through the fluid recipient line and the reinfusion branch away from the fluid recipient at least until the air in the fluid recipient line is removed from the fluid recipient line.

6. The combination of claim 5, wherein the controller is further programmed to verify that the air in the fluid recipient line has passed through the air detection assembly away from the fluid recipient during operation of the fluid recipient pump in the second direction.

7. The combination of claim 5, further comprising a processed fluid weigh scale configured to measure first and second weights of at least a portion of the fluid flow circuit and the processed fluid and/or replacement fluid therein, the first weight being measured during operation of the fluid processing system to return processed fluid and/or replacement fluid from the fluid processing chamber toward the fluid recipient and the second weight being measured when operation of the fluid recipient pump is paused, wherein the controller is further programmed to
   instruct the fluid recipient pump to pause operation in either the first direction or the second direction after the air in the fluid recipient line has been removed from the fluid recipient line,
   compare the first and second weights and
   if the first and second weights are substantially the same or if the second weight is greater than the first weight, instruct the fluid recipient pump to operate in the first direction to pump processed fluid and/or replacement fluid through the fluid recipient line toward the fluid recipient.

8. The combination of claim 7, wherein the fluid flow circuit includes a processed fluid reservoir in fluid communication with the fluid recipient line and the fluid processing chamber and configured to receive an amount of processed fluid and/or replacement fluid from the fluid processing chamber prior to the processed fluid and/or replacement fluid being returned to the fluid recipient.

9. The combination of claim 8, wherein the processed fluid weigh scale is configured to weigh the processed fluid reservoir and the processed fluid and/or replacement fluid therein.

10. The combination of claim 8, wherein the controller is programmed to instruct the fluid recipient pump to operate in the second direction to pump processed fluid and/or replacement fluid through the fluid recipient line into the processed fluid reservoir to remove the air from the fluid recipient line.

11. The combination of claim 8, wherein the controller is further programmed to, upon receiving said output,
   determine the amount of processed fluid and/or replacement fluid in the fluid recipient line between the air and the processed fluid reservoir, and
   automatically instruct the fluid recipient pump to operate in the second direction until said amount of processed fluid and/or replacement fluid in the fluid recipient line between the air and the processed fluid reservoir plus an additional amount of processed fluid and/or replacement fluid in the fluid recipient line are pumped into the processed fluid reservoir.

12. The combination of claim 5, wherein
   the fluid recipient pump is a rotatable peristaltic pump, and
   the controller is programmed to, upon receiving said output, automatically instruct the fluid recipient pump to operate in the second direction for a preselected number of rotations to remove air from the fluid recipient line.

13. A method of processing a fluid and returning processed fluid and/or replacement fluid to a fluid recipient, the method comprising
   obtaining fluid from a fluid source via a fluid recipient line;
   processing the fluid;
   controlling a fluid recipient pump to operate in a first direction to pump processed fluid and/or replacement fluid through the fluid recipient line toward a fluid recipient;
   monitoring the processed fluid and/or replacement fluid being pumped through the fluid recipient line toward the fluid recipient for the presence of air; and
   if air is detected in the processed fluid and/or replacement fluid being pumped through the fluid recipient line toward the fluid recipient, automatically controlling the fluid recipient pump to operate in a second direction to pump the processed fluid and/or replacement fluid containing air through the fluid recipient line away from the fluid recipient until the air has been removed from the fluid recipient line.

14. The method of claim 13, further comprising monitoring the processed fluid and/or replacement fluid being pumped away from the fluid recipient to verify that the air in the processed fluid and/or replacement fluid has been pumped away from the fluid recipient.

15. The method of claim 13, wherein said controlling the fluid recipient pump to operate in the first direction to pump processed fluid and/or replacement fluid through the fluid recipient line toward a fluid recipient includes pumping processed fluid and/or replacement fluid through a fluid flow circuit including the fluid recipient line, and further comprising
   measuring a first weight of at least a portion of the fluid flow circuit and the processed fluid and/or replacement fluid therein during operation of the fluid recipient pump to pump processed fluid and/or replacement fluid through the fluid recipient line toward the fluid recipient,
   pausing the flow of processed fluid and/or replacement fluid through the fluid recipient line after the air has been removed from the fluid recipient line,
   measuring a second weight of said at least a portion of the fluid flow circuit and the processed fluid and/or replacement fluid therein while the flow of the processed fluid and/or replacement fluid through the fluid recipient line is paused,
   comparing the first and second weights, and
   if the first and second weights are substantially the same or if the second weight is greater than the first weight, controlling the fluid recipient pump to pump the processed fluid and/or replacement fluid through the fluid recipient line toward the fluid recipient.

16. The method of claim 15, wherein the fluid flow circuit includes a processed fluid reservoir into which processed fluid and/or replacement fluid is pumped prior to the processed fluid and/or replacement fluid being pumped through the fluid recipient line toward the fluid recipient.

17. The method of claim 16, wherein said measuring the weight of at least a portion of the fluid flow circuit and the processed fluid and/or replacement fluid therein includes measuring the weight of the processed fluid reservoir and the processed fluid and/or replacement fluid therein.

18. The method of claim 16, wherein said automatically controlling the fluid recipient pump to operate in the second direction to pump the processed fluid and/or replacement fluid through the fluid recipient line away from the fluid recipient until the air has been removed from the fluid recipient line includes pumping the processed fluid and/or replacement fluid into the processed fluid reservoir to remove the air from the fluid recipient line.

19. The method of claim 16, further comprising
   determining the amount of processed fluid and/or replacement fluid between the air and the processed fluid reservoir, and
   automatically pumping the processed fluid and/or replacement fluid away from the fluid recipient until said amount of processed fluid and/or replacement fluid between the air and the processed fluid reservoir plus an additional amount of processed fluid and/or replacement fluid are pumped into the processed fluid reservoir.

20. The method of claim 13, wherein
   the fluid recipient pump is a rotatable peristaltic pump, and
   said automatically controlling the fluid recipient pump to operate in the second direction to pump the processed fluid and/or replacement fluid through the fluid recipient line away from the fluid recipient until the air has been removed from fluid recipient line includes operating the fluid recipient pump for a preselected number of rotations to remove the air from the fluid recipient line.

* * * * *